(12) United States Patent
Tymoshenko et al.

(10) Patent No.: US 8,700,589 B2
(45) Date of Patent: Apr. 15, 2014

(54) SYSTEM FOR LINKING MEDICAL TERMS FOR A MEDICAL KNOWLEDGE BASE

(75) Inventors: Kateryna Tymoshenko, Trento (IT); Swapna Somasundaran, Lawrenceville, NJ (US); Vinay Damodar Shet, Princeton, NJ (US)

(73) Assignee: Siemens Corporation, Iselin, NJ (US)

( * ) Notice: Subject to any disclaimer, the term of this patent is extended or adjusted under 35 U.S.C. 154(b) by 47 days.

(21) Appl. No.: 13/479,388

(22) Filed: May 24, 2012

(65) Prior Publication Data

US 2013/0066903 A1 Mar. 14, 2013

Related U.S. Application Data

(60) Provisional application No. 61/533,412, filed on Sep. 12, 2011, provisional application No. 61/602,636, filed on Feb. 24, 2012.

(51) Int. Cl.
*G06F 17/21* (2006.01)
*G06F 17/30* (2006.01)
*G06F 17/00* (2006.01)

(52) U.S. Cl.
CPC ... *G06F 17/30705* (2013.01); *Y10S 707/99933* (2013.01)
USPC ...................... 707/705; 707/706; 707/999.003

(58) Field of Classification Search
USPC .................................. 707/706, 707, 999.003
See application file for complete search history.

(56) References Cited

U.S. PATENT DOCUMENTS

| 8,265,925 B2 * | 9/2012 | Aarskog | 704/9 |
| 2010/0114561 A1 * | 5/2010 | Yasin | 704/9 |

OTHER PUBLICATIONS

Cartic Ramakrishnan, et al., "A Framework for Schema-Driven Relationship Discovery from Unstructured Text", The Semantic Web-ISC 2006, pp. 583-596, 2006.
Asma Ben Abacha and Pierre Zweigenbaum, "A Hybrid Approach for the Extraction of Semantic Relations from Medline Abstracts", In Proceedings of the 12th international conference on Computational linguistics and intelligent text processing—vol. Part II, pp. 139-150. Springer-Verlag, 2011.
Asma Ben Abacha and Pierre Zweigenbaum, "Automatic extraction of semantic relations between medical entities: a rule based approach", Journal of Biomedical Semantics, 2(Suppl 5): S4, 2011.
B. Rosario and M.A. Hearst, "Classifying semantic relations in bioscience texts". In Proceedings of the 42nd annual meeting on association for computational lin-guistics, pp. 430-es. Association for Computational Linguistics, 2004.

(Continued)

*Primary Examiner* — Baoquoc N To
(74) *Attorney, Agent, or Firm* — Joshua B Ryan (57) ABSTRACT

A system generates medical knowledge base information by using predetermined data source specific message syntax information in identifying first and second information received from first and second data sources respectively. The first and second information indicates at least one type of medical relationship between the received first and second medical terms. The system determines likelihood of existence of the at least one type of medical relationship indicated by a combination of the first and second information, in response to predetermined information indicating a number of occurrences of the at least one type of relationship in data of at least one of the first and second data source. The system outputs first and second medical terms and the at least one type of medical relationship in response to the determined likelihood of existence.

21 Claims, 10 Drawing Sheets

| 303 | 305 |
|---|---|
| may_treat | Drug A may treat disease B |
| may_prevent | Drug A may prevent disease B |
| may_diagnose | Drug A may diagnose disease B |
| has_Ingredient | Drug A has ingredient B |
| has_MoA | Drug A has mechanism of action B |
| has_PE | Drug A has physiological effect B |
| induces | Drug A induces disease B |
| CI_with | Drug A is contraindicated (known to cause adverse reaction) with disease B |
| CI_MoA | Drug A is contraindicated with mechanism of action of drug B |
| CI_ChemClass | Drug A is contraindicated with chemical class of drug B |

(56) References Cited

OTHER PUBLICATIONS

L. Yao, S. Riedel, and A. McCallum, "Collective Cross-Document Relation Extraction Without Labelled Data", In Proceedings of the 2010 Conference on Empirical Methods in Natural Language Processing, pp. 1013-1023. Association for Computational Linguistics, 2010.
Saurav Sahay, et al., "Discovering Semantic Biomedical Relations Utilizing the Web", ACM Trans. Knowledge Discovery. Data, 2:3:1-3:15, Apr. 2008.
Mike Mintz, Steven Bills, Rion Snow, Dan Jurafsky, "Distant Supervision for relation extraction without labeled data", In Proceedings of the Joint Conference of the 47th Annual Meeting of the ACL and the 4th International Joint Conference on Natural Language Processing of the AFNLP: vol. 2-vol. 2, pp. 1003-1011. Association for Computational Linguistics, 2009.
Truc-Vein, T. Nguyen and Alessandro Moschitti, "End-to-End Relation Extraction Using Distant Supervision from External Semantic Repositories", In Proceedings of the 49th Annual Meeting of the Association for Computational Linguistics: Human Language Technologies: short papers—vol. 2, pp. 277-282. Association for Computational Linguistics, 2011.
Y.S. Chang and Dan Roth, "Exploiting Background Knowledge for Relation Extraction", In Proceedings of the 23rd International Conference on Computational Linguistics, pp. 152-160. Association for Computational Linguistics, 2010.
C. Giuliano, A. Lavelli, and L. Romano, "Exploiting shallow linguistic information for relation extraction from biomedical literature", In Proceedings of the Eleventh Conference of the European Chapter of the Association for Computational Linguistics (EACL-2006), pp. 401-408, 2006.
Oana Frunza and Diana Inkpen, "Extraction of Disease-Treatment Semantic Relations from Biomedical Sentences", In Proceeding of the 2010 Workshop on Biomedical Natural Language Processing, pp. 91-98. Association for Computational Linguistics, 2010.
J. Li, Z. Zhang, X. Li, and H. Chen, "Kernel-based learning for biomedical relation extraction", Journal of the American Society for Information Science and TEchnology, 59(5): 756-769, 2008.
Raphael Hoffman, Congle Zhang, Daniel S. Weld, "Learning 5000 Relational Extractors", In Proceedings of the 48th Annual Meeting of the Association for Computational Linguistics, pp. 286-295. Association for Computational Linguistics, 2010.
Philippe Thomas, et al., "Learning to Extraction Protein-Protein Interactions using Distant Supervision", In Proceedings of Workshop on Robust Unsupervised and Semisupervised Methods in Natural Language Processing, pp. 25-32, Hissar, Bulgaria, Sep. 2011.
Chih-Chung Change and Chih-Jen Lin, "A Library for support vector machines", ACM Transactions on Intelligent Systems and Technology, 2:27:1-27:27, 2011. Software available at http://www.csie.ntu.edu.tw/~cjlin/libsvm.
Gyorgy Szarvas and Iryna Gurevych, "TUD: semantic relatedness for relation classification", In Proceedings of the 5th International Workshop on Semantic Evaluation, pp. 2010-213. Association for Computational Linguistics, 2010.
US co-pending patent application titled "A System for Generating a Medical Knowledge Base" filed on May 24, 2012.

* cited by examiner

Figure 1

| Drugs | Diseases |
| --- | --- |
| Drug Pharmacology Class | Drug Physiological Effects |
| Drug Ingredients | Drug Mechanism of Action |

| | |
|---|---|
| may_treat | Drug A may treat disease B |
| may_prevent | Drug A may prevent disease B |
| may_diagnose | Drug A may diagnose disease B |
| has_Ingredient | Drug A has ingredient B |
| has_MoA | Drug A has mechanism of action B |
| has_PE | Drug A has physiological effect B |
| induces | Drug A induces disease B |
| CI_with | Drug A is contraindicated (known to cause adverse reaction) with disease B |
| CI_MoA | Drug A is contraindicated with mechanism of action of drug B |
| CI_ChemClass | Drug A is contraindicated with chemical class of drug B |

| Name | Description | Count |
|---|---|---|
| CI ChemClass | has contraindicated structural chemical class | 1,113 |
| CI MoA | has contraindicated mechanism of action | 319 |
| CI with | has therapeutic or co-morbid contraindication with | 15,702 |
| has Ingredient | has chemical ingredient | 2,103 |
| has MoA | has method of action | 6,561 |
| has PE | has functional activity | 10,452 |
| induces | induces | 273 |
| may diagnose | may diagnose | 486 |
| may prevent | may prevent | 882 |
| may treat | may treat | 13,245 |
| NOREL | no relation | 51,988 |
| Overall | | 103,124 |

Figure 7

|  | ensemble | ST | STCUI | DS |
|---|---|---|---|---|
| count | 51074 | 51016 | 51016 | 2714 |
| p | 91.76 | 63.25 | 90.19 | 73.57 |
| r | 91.69 | 67.22 | 90.71 | 76.12 |
| F₁ | 91.73 | 65.18 | 90.45 | 74.82 |
| Accuracy | 94.14 | 77.2 | 93.03 | 2.19 |

Figure 8

| Relation name | Best performing feature set |
|---|---|
| CI ChemClass | umlsPF:::SNOMEDCT, umlsSemType, umlsCUI |
| CI MoA | wikiCategory, sectStrongLinkCat |
| CI with | umlsPF:::SNOMEDCT, umlsSemType, wikiCategory, pairwiseLinkFeatures, sectLinkSectPath, umlsCUI |
| has Ingredient | umlsPF:::MEDCIN, umlsSemType, wikiCategory, pairwiseLinkFeatures, sectLinkSectPath |
| has MoA | wikiCategory, pairwiseLinkFeatures, sectLinkSectPath, umlsCUI |
| has PE | umlsPF:::SNOMEDCT, wikiCategory, pairwiseLinkFeatures, sectLinkSectPath |
| induces | umlsPF:::SNOMEDCT, umlsSemType, umlsCUI |
| may diagnose | umlsPF:::SNOMEDCT, umlsSemType, umlsCUI |
| may prevent | umlsPF:::SNOMEDCT, umlsCUI |
| may treat | umlsPF:::SNOMEDCT, umlsSemType, umlsCUI |
| Overall | umlsSemType, umlsCUI |

Figure 9

| Relation name | Best performing feature set | | | | STCUI | | | | DS | | | |
|---|---|---|---|---|---|---|---|---|---|---|---|---|
| | count | p | r | f | count | p | r | f | count | p | r | f |
| CI ChemClass | 939 | 92.05 | 94.89 | 93.45 | 1113 | 91.42 | 92.81 | 92.11 | 94 | 58.70 | 86.17 | 69.83 |
| CI MoA | 115 | 94.07 | 96.52 | 95.28 | 318 | 88.99 | 94.03 | 91.44 | 0 | 0.00 | 0.00 | 0.00 |
| CI with | 5177 | 92.13 | 94.3 | 93.2 | 15645 | 89.84 | 93.61 | 91.69 | 599 | 90.32 | 32.72 | 48.04 |
| has Ingredient | 134 | 81.25 | 67.91 | 73.98 | 2081 | 67.66 | 43.44 | 52.91 | 47 | 69.57 | 34.04 | 45.71 |
| has MoA | 951 | 94.34 | 96.42 | 95.37 | 6549 | 95.28 | 95.21 | 95.24 | 31 | 75.00 | 87.10 | 80.60 |
| has PE | 26 | 100 | 100 | 100 | 10449 | 95.59 | 96.35 | 95.97 | 85 | 90.91 | 82.35 | 86.42 |
| induces | 196 | 90.66 | 84.18 | 87.3 | 273 | 87.44 | 71.43 | 78.63 | 47 | 0.00 | 0.00 | 0.00 |
| may diagnose | 184 | 82.14 | 62.5 | 70.99 | 483 | 89.74 | 56.11 | 69.04 | 17 | 100.00 | 11.76 | 21.05 |
| may prevent | 598 | 83.7 | 69.57 | 75.98 | 882 | 78.03 | 55.56 | 64.9 | 136 | 48.00 | 8.82 | 14.91 |
| may treat | 10038 | 87.95 | 93.47 | 90.63 | 13223 | 86.82 | 91.77 | 89.23 | 1741 | 72.60 | 99.08 | 83.80 |
| Overall | 51016 | 90.19 | 90.71 | 90.45 | 51016 | 90.19 | 90.71 | 90.45 | 2797 | 73.57 | 76.12 | 74.82 |

FIGURE 10

SYSTEM FOR LINKING MEDICAL TERMS FOR A MEDICAL KNOWLEDGE BASE

This is a non-provisional application of provisional application Ser. No. 61/533,412 filed on 12 Sep. 2011 and provisional application Ser. No. 61/602,636 filed on 24 Feb. 2012, by S. Somasundaran et al.

FIELD OF THE INVENTION

This invention concerns a system for generating medical knowledge base information by interrogating different data sources to determine whether a medical relationship occurs between different terms in data of the different data sources and by using predetermined relationship occurrence related information.

BACKGROUND OF THE INVENTION

Medical knowledge bases that capture information about medical entities can be used by reasoning engines and question answering applications to assist medical practitioners. Medical entities are terms representing concepts and events such as diseases, treatments, symptoms and drugs, for example. Typical medical knowledge about these entities includes information about their properties, as well as their relationships with other medical concepts. For example, knowledge about a disease includes its symptoms, treatments, complications and drugs that treat it and includes the relationship of the disease to entities such as drugs and treatments. Similarly, knowledge about a drug includes its relationship to the diseases it treats, its side effects, and its relationship and interactions with other drugs. Thus, relationships between medical entities are needed for constructing comprehensive knowledge bases for them. One way to create knowledge bases is by using a human user encoder to encode his/her knowledge. However, as this process is manually intensive, it is expensive, slow, tedious, and suffers from a lack of wide coverage.

Clinical decision support (CDS) systems acquire data from patient health records and identify and flag potentially adverse drug interactions. Adverse drug interactions may occur due to a wide variety of factors involving active and non-active ingredients of drugs, their mechanisms of actions within the body, their physiological effects, contraindications with certain conditions, among others. While there exist multiple knowledge sources designed for human use, this data is not in a directly machine readable form. Structured knowledge sources like ontologies, conversely, typically lack adequate coverage to build robust CDS systems. Manually encoding knowledge, to make up for this lack of coverage, is both tedious and expensive. A system according to invention principles addresses these deficiencies and related problems.

SUMMARY OF THE INVENTION

A system according to invention principles automatically or partially automatically interrogates multiple data sources to identify a medical relationship between terms such as diseases, drugs, and their functional effects and actions, with a high level of confidence. A system generates medical knowledge base information. A data processor, in response to receiving first and second different medical terms, automatically, forms multiple query messages in data source specific formats for querying corresponding multiple different data sources for information indicating a potential medical relationship between the received first and second medical terms. The data processor uses predetermined data source specific message syntax information in identifying first and second information received from first and second data sources respectively. The first and second information indicates at least one type of medical relationship between the received first and second medical terms. The data processor determines likelihood of existence of the at least one type of medical relationship indicated by a combination of the first and second information, in response to predetermined information indicating a number of occurrences of the at least one type of relationship in data of at least one of the first and second data sources. Predetermined information comprises predetermined knowledge concerning collocations of combinations of first and second information together with a correct medical relationship. Specifically, this is predetermined knowledge about medical relationships between two entities along with knowledge of first and second information for these entities. The predetermined knowledge about entities' relationship is obtained from an external data source. An output processor outputs data representing the first and second medical terms and the at least one type of medical relationship in response to the determined likelihood of existence.

DETAILED DESCRIPTION OF THE INVENTION

The system advantageously extends a knowledge base and improves its precision and recall. In one embodiment, the system employs large-scale text mining with user human interaction to reduce the time and effort for a human user encoder by automatically extracting relevant knowledge and presenting it to the user for selection. The system automatically discovers medical concepts that are related to a medical entity and determines the type of relationships potentially existing between an entity and discovered entities. This is achieved by mining for knowledge about medical concepts of interest in large (or other) sources of information. The system uses contextual, semantic information of multiple knowledge sources in determining relationships between medical entities. In one embodiment, the system automatically searches for an entity (term) in large unstructured databases, retrieves relevant sentences, recognizes other entities in these sentences, and uses knowledge within and outside the sentences to form a hypothesis about the relationship between the given entity and the co-occurring entities. The words "entity" and "term" are used interchangeably herein to indicate a sequence of one or more medically related words or text strings. The system creates overall aggregate predictions concerning the relationships for a given entity and presents the predictions to a user (e.g., an expert in the field). The user can either accept or reject system predictions. The system also provides a user with a prediction confidence indicator and additional information discovered via mining in order to assist the user. Thus the system reduces burden on a user whilst facilitating improved medical knowledge base coverage and precision.

Known systems lack a comprehensive human-annotated corpus. The system uses entity semantic information and linkage properties of entity-pairs in common knowledge resources. For example, Aspirin, a drug, has a property of being anti-inflammatory. Anti-inflammatory drugs are generally useful for treating pain. Thus, by using the knowledge of the property of Aspirin and the knowledge that Headache is a type of pain, it is inferred that there is likely to be a "may treat" relationship between Aspirin and Headache. The system employs a human-curated ontology such as the National Drug File (NDF) as a resource for standard annotations for relationships between medical entities. The system also uses various resources such as Wikipedia and the Unified Medical Language System (UMLS), and statistical methods to generate knowledge base information.

The system in one embodiment, encodes semantic features such as entity-category and taxonomy (derived from Wikipedia, SNOMED-CT (Systematized Nomenclature of Medicine—Clinical Terms), for example), entity-pair linkage (derived from Wikipedia), into a machine learning method. The system employs different relationship classifiers and combines different individual predictions to provide a composite (ensemble) result. The system is tested using approximately 100,000 entity pairs and ten medical relationships confirming improvement in knowledge base coverage and precision.

Figure 1:
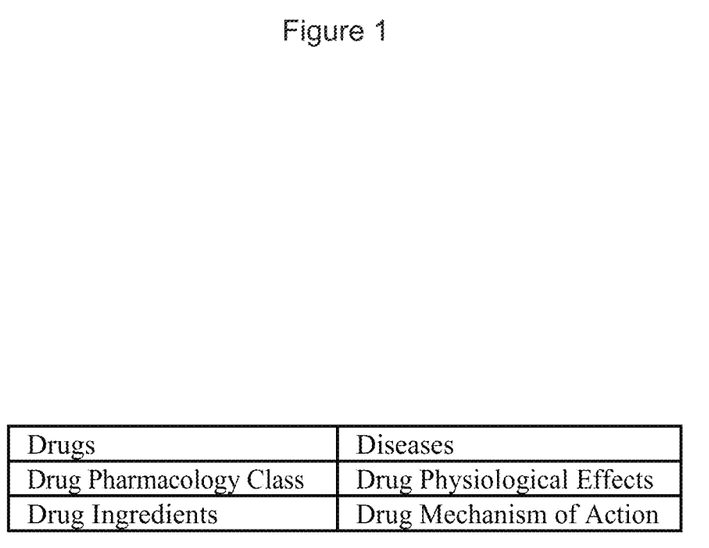
FIG. 1 shows a Table indicating medical entities.
Figure 3:
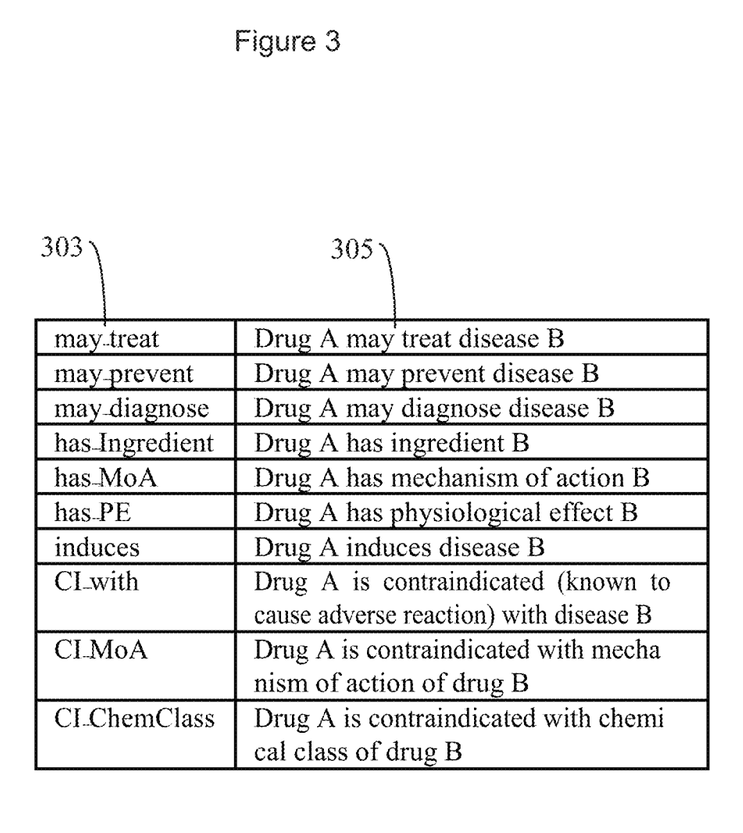
FIG. 3 shows a Table indicating medical entity relationships.

FIG. 1 shows a Table indicating medical entities (drugs, diseases, drug pharmacology class, drug physiological effects, drug ingredients and drug mechanism of action). FIG. 3 shows a Table indicating medical entity relationships in column 303 and corresponding relationship description in column 305. The system uses entity semantics, such as, entity classes, taxonomical information about the entities, the way knowledge resources describe and link the entities to identify type of relationship that may exist between two terms (entities). Entity categories (and taxonomic information) and their characteristics are used in relationship identification. For instance, for the entity pair Aspirin-Headache, the first piece of information (Aspirin belongs to a non-inflammatory class of drugs in most medical knowledge bases) can be obtained using category information in Wikipedia, for example. The second piece of information (non-inflammatory drugs are useful for treating pain) is learnt by the system from a training dataset where another member of the non-inflammatory class (e.g. Ibuprofen) is in a treats relationship with a pain symptom (e.g. headache).

The system also uses the way knowledge resources represent and link entities to identify a type of relationship between an entity pair. For instance, a Wikipedia page for Ibuprofen mentions a symptom Fever in the section on "Medical Uses". Similarly, a "Medications" section for Fever mentions the entity Ibuprofen. Using such examples, the system adaptively learns that if an entity E1 occurs in the medical uses of another entity E2, then E2 most likely treats (or prevents) E1. Similarly, the links that connect the entities (in taxonomies or Wikipedia) are used to identify a type of interaction that exists between them.

The system automatically mines large datasets to discover other entities that co-occur with a particular entity (that is, that occur in the same sentence as this entity) and uses different classifiers to establish relationships between the particular entity and the discovered entities. In other embodiments, the system automatically mines large datasets to discover other entities that co-occur, i.e., that occur together in other text segments such as sentence portions, paragraphs, pages, for example. An input to a medical knowledge base information generation system comprises data indicating entities (e.g., MI, Myocardial Infarction) for which knowledge is to be built. The output of the system comprises a list of tuples (term pairs) encoding information concerning input. A tuple is represented as relation (entity1, entity2), where entity1 (or entity2) is the entity of interest and relationship describes the manner in which the two are related. The list of tuples and associated sentences are presented to a user for review, rejection or acceptance and in response to acceptance, addition to a knowledge base.

Figure 2:
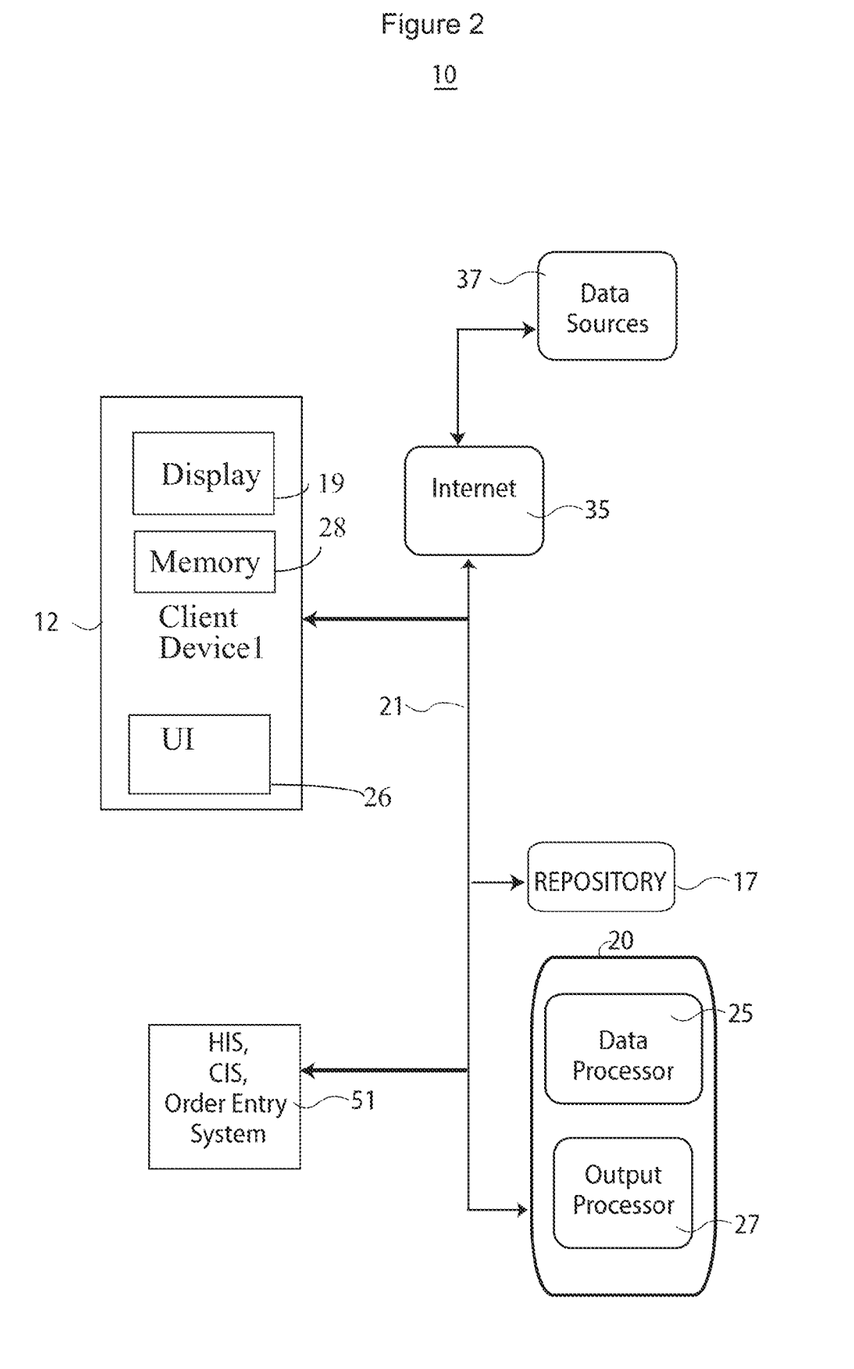
FIG. 2 shows a system for generating medical knowledge base information, according to an embodiment of the invention.

FIG. 2 shows system 10 for generating medical knowledge base information. System 10 includes one or more processing devices on network 21 (e.g., workstations, computers or portable devices such as notebooks, Personal Digital Assistants, phones) 12 that individually include a user interface 26 enabling user interaction with a Graphical User Interface (GUI) and display 19 supporting GUI and medical data, image and administrative information presentation in response to predetermined user (e.g., physician, nurse administrator) specific preferences. System 10 also includes at least one repository 17, server 20 and Healthcare Information System (HIS) 51 (including ADT, clinical information, order entry and other applications) intercommunicating via network 21. Server 20 includes data processor 25 and output processor 27. Server 20 communicates via network 21 and Internet (or an intra-net) 35 (or via Internet 35 directly, connection not shown to preserve drawing clarity) with data sources 37. At least one repository 17 comprises information including, relationship semantics data, relationship classifier training data, patient medical record data, hospital transaction message data, medical treatment information, medical ontologies, medical dictionaries, medical texts and guidelines, general medical encyclopedic knowledge resources and user preferences. Repository 17 also includes predetermined medical terms, predetermined semantic information in one or more different repositories used to identify a medical relationship in response to meaning and definition of a first and different second term and predetermined sentence structure and syntax rules, for example.

Data processor 25 in response to receiving first and second different medical terms, automatically forms multiple query messages in data source specific formats for querying corresponding multiple different data sources 37 for information indicating a potential medical relationship between the received first and second medical terms. Processor 25 uses predetermined data source specific message syntax information in repository 17 in identifying first and second information received from first and second data sources respectively. Before only multiple data sources and first and second information were mentioned. I'm marking with yellow colour all the following occurrences of data source mentions, which confuse me]. The first and second information indicates at least one type of medical relationship between the received first and second medical terms. Processor 25 determines likelihood of existence of the at least one type of medical relationship indicated by the first data source, in response to predetermined information indicating a number of occurrences of the at least one type of relationship in data of the first data source. Output processor 27 outputs data representing the first and second medical terms and the at least one type of medical relationship in response to the determined likelihood of existence.

Figure 4:
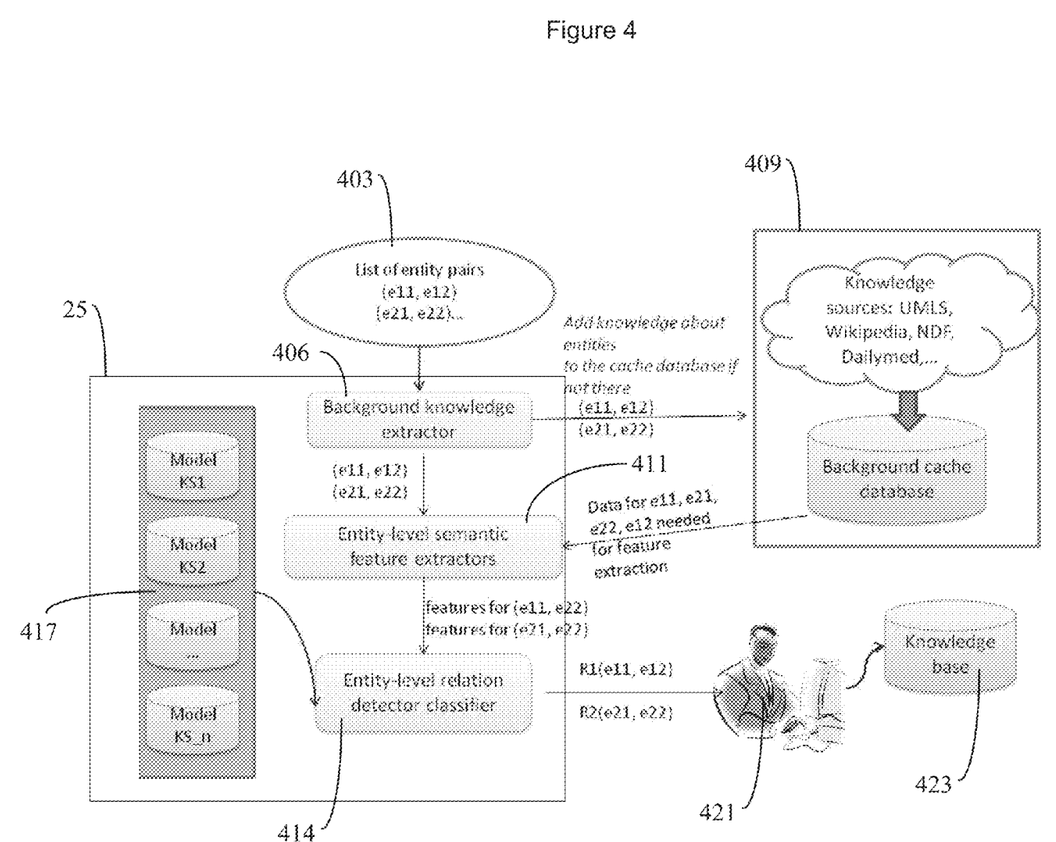
FIG. 4 shows a system and process flow for generating medical knowledge base information by interrogating different data sources to determine whether a medical relationship occurs between different terms in data of the different data sources and by using predetermined relationship occurrence related information, according to an embodiment of the invention.

FIG. 4 shows a system and process flow for generating medical knowledge base information by interrogating different data sources to determine features, characteristics and properties indicative of a medical relationship occurring between different terms by using predetermined relationship occurrence related information. Data processor 25 (FIG. 1) receives (403) a pair of first and second different medical terms and employs Background Knowledge Extractor 406 for extracting information indicating a potential medical relationship between the received first and second medical terms by interrogating multiple knowledge resources 409. Extractor 406 automatically forms multiple query messages in data source specific formats for querying corresponding multiple different data sources 409 for information indicating a potential medical relationship between the received first and second medical terms.

Feature extractor 411 of processor 25 uses predetermined data source specific message syntax information in identifying first and second information items received from data sources 409 and provides relationship information items to classifier 414. Classifier 414 processes the information items indicating a potential medical relationship between the received first and second medical terms using semantic information received from sources 409 and previously trained learning models 417 to identify a potential medical relationship. Classifier 414 uses previously trained learning models 417 to provide a statistical prediction of a medical relationship. Learning models 417 determine likelihood of existence of a medical relationship indicated by a particular data or a combination of data sources, in response to predetermined information indicating a number of occurrences of the at least one type of relationship in data of the particular data source, for example. An output processor 27 outputs data representing the first and second medical terms and an identified medical relationship determined by classifier 414 for review by user 421 and upon acceptance, update of knowledge base 423. In one embodiment classifier 414 automatically updates knowledge base 423 without user interaction.

Figure 5:
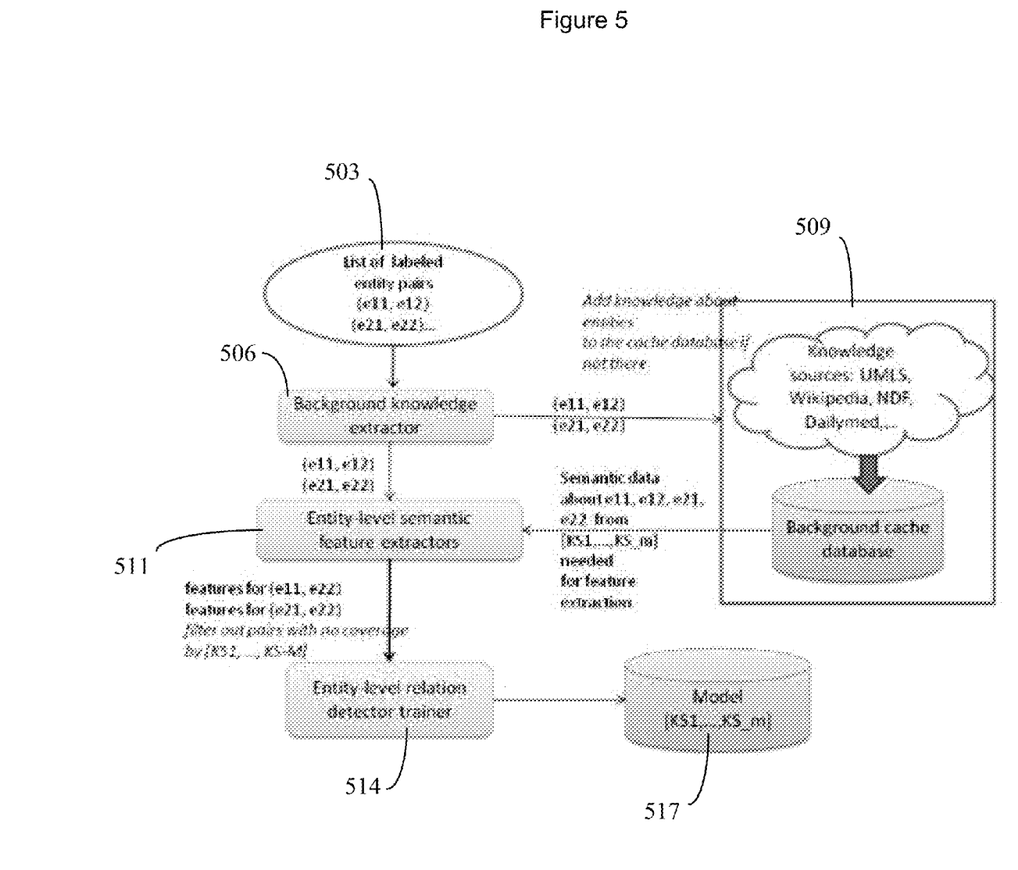
FIG. 5 shows a system and process flow for training a classifier for determining whether a medical relationship occurs between different terms using predetermined relationship occurrence related information, according to an embodiment of the invention.

FIG. 5 shows a system and process flow employed by processor 25 for training a classifier for determining whether a medical relationship occurs between different terms using predetermined relationship occurrence related information. Data processor 25 (FIG. 1) receives (503) a pair of first and second different medical terms having a known relationship. Background Knowledge Extractor 506 extracts information indicating a potential medical relationship between the received first and second medical terms by interrogating multiple knowledge resources 509. Extractor 506 automatically forms multiple query messages in data source specific formats for querying corresponding multiple different data sources 509 for information indicating a potential medical relationship between the received first and second medical terms.

Feature extractor 511 of processor 25 uses predetermined data source specific message syntax information in identifying first and second information items received from data sources 509 and provides relationship information items to classifier generator 514. Classifier generator 514 processes the information items indicating a potential medical relationship between the received first and second medical terms using semantic information received from sources 509 and previously trained learning models 517 to identify a potential medical relationship. Classifier 514 uses previously trained learning models 517 to provide a statistical prediction of a medical relationship. The predicted relationship provided by classifier generator 514 is compared with the known relationship and learning models are updated and corrected in response to the comparison. Classifier generator 514 creates a classifier using information received from data sources 509 for entity pair 503 having a known relationship. Classifiers 517 are trained using semantic features 509 extracted for the pair 503 and the known relationship of pair 503.

Data sources 409 (FIG. 4), 509 (FIG. 5) include, for example, Wikipedia, UMLS semantic network, and selected UMLS metathesaurus sources for extracting semantic features, MEDCIN, SNOMED CT and MeSH, for example. Wikipedia is an online multilingual encyclopedia collaboratively created by volunteers. A Wikipedia article describes a specific concept or an entity. Each Wikipedia page is assigned one or more categories reflecting its topic. The categories are organized into a taxonomic system with parent/child (broader/narrower) relations. Long articles are split into sections with titles Important words, crucial for understanding, e.g. scientific terms, are assigned an internal link pointing to other Wikipedia pages, explaining the meaning of the concept meant by the word.

UMLS metathesaurus incorporates multiple medical terminologies, taxonomies and vocabularies. Moreover, UMLS contains a table, which stores information about a path from a certain concept to a root in a taxonomy of a specific source, path-to-root. The sources MEDCIN, SNOMED-CT and MeSH have broad medical terminology coverage. MEDCIN is a medical terminology comprising a standardized vocabulary for describing diagnoses, symptoms, conditions, therapy, tests and history. SNOMED CT (Systematized Nomenclature of Medicine—Clinical Terms) is a medical terminology including hierarchically organized medical terms describing clinical findings, organisms, procedures and pharmaceutical products. MeSH (Medical Subject Headings) is a controlled vocabulary for indexing biomedical literature containing hierarchically organized subject headings or descriptors, e.g. Antithrombins, their qualifiers, e.g. synthesis, and synonym information. The UMLS semantic network describes semantic types of concepts in biomedical domain, e.g. enzyme, vitamin, steroid, and the relationships between these categories. Each UMLS concept is typically assigned one or more UMLS semantic network types. The semantic features may be broadly categorized as category/taxonomy-based features, and linkage-based features. A WordNet data source is also interrogated.

The semantic features capture the class properties of the individual entities. The categories and taxonomy features are extracted from the data sources and represent topical and semantic class information about the entities. The Wikipedia category features, wikicategory, are extracted by mapping each of the entities $e_1$ and $e_2$ in a given entity pair to their respective Wikipedia pages $p_1$ and $p_2$ (a string match is used for page retrieval). Categories of $p_1$ and $p_2$ and their ancestors in the Wikipedia category taxonomy up to two levels up are used as features. For example, an Aspirin page has categories Acetate_esters and Antiplatelet_drugs.

A core unit of UMLS is a concept, which is uniquely identified by a concept unique identifier (CUI). This is similar to a category feature in Wikipedia. From UMLS sources (MEDCIN, SNOMED, MeSH), the system extracts taxonomy features, umlsPF:MEDCIN, relationships PF::SNOMED and relationships PF::MeSH respectively. The taxonomy features capture the path information from the root to the parent of the concept (the concept itself is not included in the path feature). The UMLS semantic types of both entities of an input pair are used in determining their interactions.

Linkage-based features are extracted from Wikipedia, for example. A pairwiseLinkFeature, captures whether each of the entity pages $p_1$ and $p_2$ in Wikipedia point to the other. Additionally, the system captures section names in which a linkage occurs. For example, aspirin and headache are in a "may treat" relation. A link to an Aspirin page occurs in a Medications section of a Fever page, while a reverse link occurs in a Medical uses section of the Aspirin page. The system captures a sectLinkSectPath feature comprising a path of sections of $p_1$ and $p_2$ that contain a common outgoing link. For instance, Abciximab has counter indications for Thrombocytopenia, and the set of sectLinkSectPath features for this pair includes, Side effects:::Causes, First paragraph:::First paragraph, First paragraph:::Medication-induced.

The system encodes features indicating strong relationships between concepts. For example, if a page for entity $e_1$ points to a page for entity $e_2$ and vice versa, this is captured by the system along with the section in which this linkage occurs. The system in one embodiment, extracts an experimental dataset from a National Drug File (NDF). NDF comprises a list of drugs released by U.S. Department of Veterans Affairs, Veterans Health Administration (VHA), which contains information about drugs and their relationships with other biomedical entities, including interactions, physiological effects, methods of action and effects. The dataset is a set of labeled examples. An example is a triple ($e_1$; R; $e_2$), where $e_1$ (subject) and $e_2$ (object) are UMLS data source concepts referred to by concept unique identifier (CUI), and R is the NDF relationship between them. If entities are not related, then R=NOREL, and such example is called a negative example. Otherwise it is positive.

Figure 6:
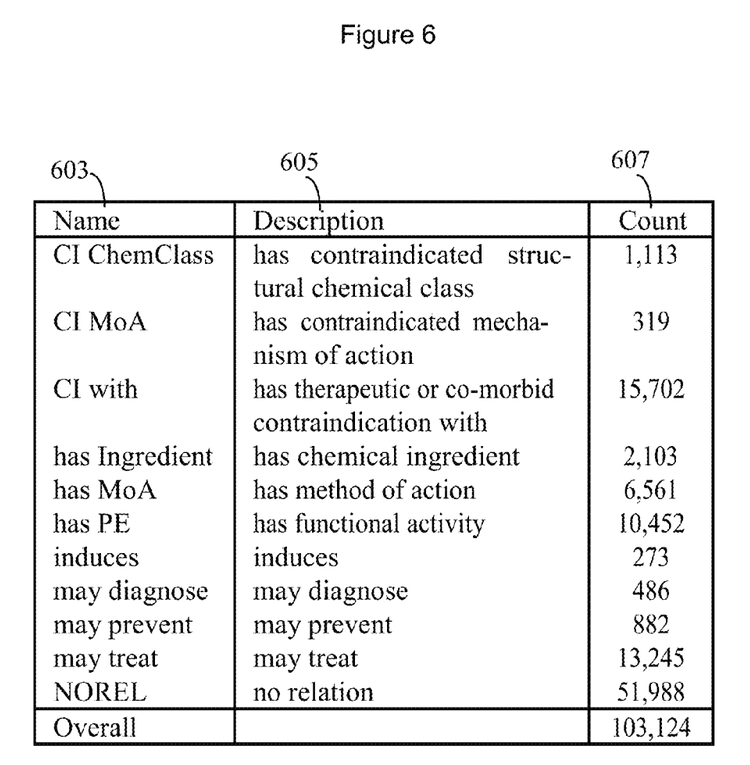
FIG. 6 shows a Table presenting numbers of particular types of medical relationship detected by interrogating a particular data source, according to an embodiment of the invention.

FIG. 6 shows a Table presenting numbers (in column 607) of ten individual particular types of most frequently used medical relationships (labeled in column 603 and described in column 605) that are detected by interrogating a particular data source (the NDF) for the relationships. The system extracts positive examples by searching the NDF for entity pairs engaged in a particular relationship. The system discards relationship examples with $e_1$ and $e_2$ connected by more that one relationship, in order not to have multiple labels per instance. In addition, the system discards triples where surface forms of subject and object contained special symbols like "%", ",", "/", as for such triples PubMed or Wikipedia coverage, for example, is low. The system randomly generates an equal amount of negative examples based on a closed world assumption. In response to a random entity pair ($e_1$; $e_2$) selection, the system determines whether NDF file contains information about a relationship between them. If it does not, then the entity pair is considered a valid example of a negative relation termed NOREL. The resulting dataset, AUTONDF contains 51,074 positive and 51,988 negative relationships. A tuple is a pair of CUIs of entities, and a relationship label.

Three classifier systems are used in one example of operation including, (i) an ST classifier trained on relationships between UMLS semantic network types, (ii) an STCUI classifier trained on relationships CUI features and (iii) a Distant Supervision system (DS). The first two systems comprise semantic network types that employ a set of features typically exploited in biomedical literature. System (i) is likely to capture the most frequently occurring relationship between specific UMLS semantic network categories. The number of negative examples is slightly larger as initially positive instances are extracted from the NDF relationships, however some of the relationships are excluded as being infrequent. System (ii) also captures the most frequent relationship per specific entities, e.g. for Aspirin this is a "may treat" relationship and compared to system (i) facilitates understanding whether more fine-grained semantic information is useful for relationship extraction. System (i) facilitates understanding whether or not improvements obtained by fine-grained semantic features is due to their sparsity, which results in a set of features uniquely identifying a specific entity. The system uses other features (resources) and feature combinations to generate a variety of different classifiers.

DS is a supervised system that predicts a relationship given two entities and their occurrence in the context of a sentence. A labeled training set for a DS system is extracted from a PubMed data source hypothesis (e.g., "if entities $e_1$ and $e_2$ are known to be in relationship R, a sentence containing a mention of both $e_1$ and $e_2$ expresses the relationship R"). The system queries PubMed for abstracts and titles containing pairs of entities from a dataset and labeled sentences containing $e_1$ and $e_2$ with relationship R. System performance is evaluated by cross-validation of the generated AUTONDF dataset. The system trains a classifier employing a specific feature set with covered instances from the AUTONDF dataset. Covered instances are where values of features from the set are known. For example, if a classifier is being trained using a Wikipedia-based feature set, both $e_1$ and $e_2$ need corresponding articles in Wikipedia. Otherwise they are skipped. The system is tested on feature sets described previously as well as their combinations involving concatenated corresponding individual feature vectors. An ensemble (composite) classifier for an i-th test cross validation is trained on outputs obtained by individual classifiers on 1, 2, i−1, i+1; 10-th tests.

System performance is evaluated in terms of precision (p), recall (r), harmonic $f_1$ measures and accuracy, for a specific feature set, e.g., when testing a classifier of the AUTONDF dataset, for example, $$F1 = \frac{2PR}{P+R} = \frac{2}{\frac{1}{R} + \frac{1}{P}}$$

Where F1 is Fmeasure, a harmonic mean of precision and recall, P is Precision comprising (true positive)/(true positive+false positive) and R is Recall comprising (true positive)/(true positive+false negative). The instances uncovered are removed. Accuracy is evaluated on a set of instances contained in a test set in a specific cross-validation test. If an entity pair is not covered by a system trained on a specific feature set, then the prediction is deemed wrong.

Figure 7:
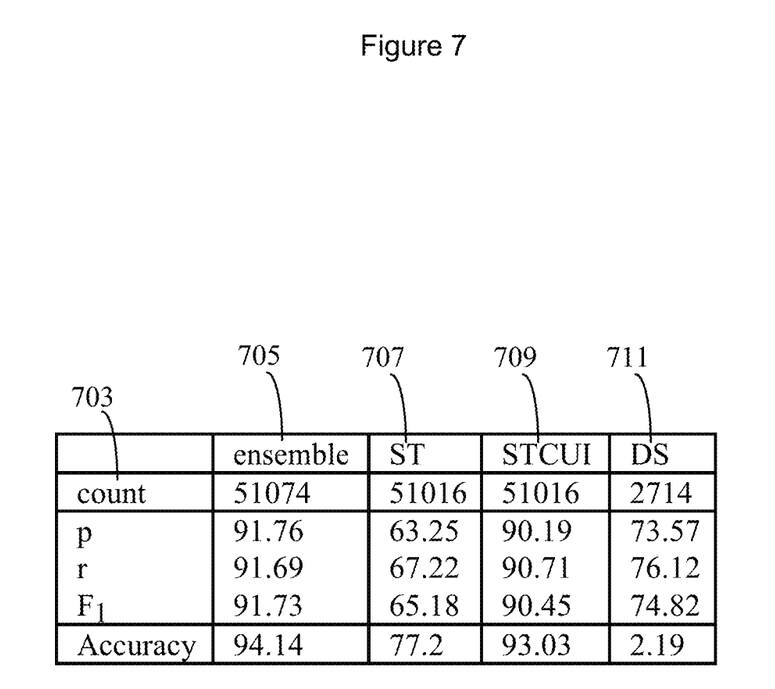
FIG. 7 shows a Table presenting indicators of performance of a classifier in relationship identification, according to an embodiment of the invention.
Figure 8:
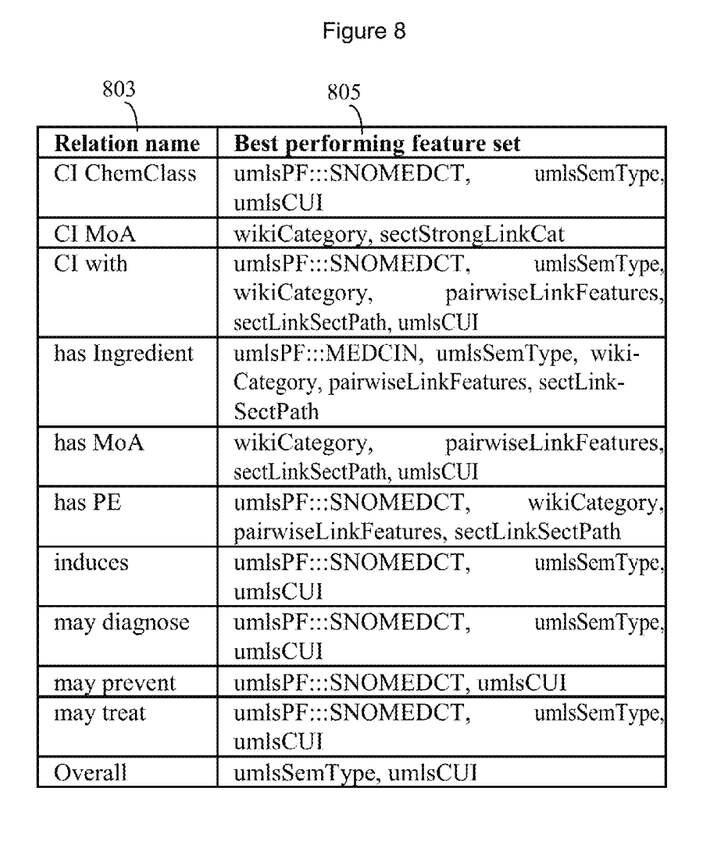
FIG. 8 shows a Table identifying best classifiers for classifying a medical relationship as being of a particular type, according to an embodiment of the invention.

FIG. 7 shows a Table presenting indicators of performance of a classifier in relationship identification of the AUTONDF dataset. The precision (p), recall (r), harmonic $f_1$ measures identified in column 703 are shown for ensemble, ST and STCUI and DS classifiers in columns 705, 707, 709 and 711 respectively. The ensemble classifier receives candidate relationship identification data as inputs from multiple different e.g., ST and STCUI classifiers. Relationship predictions of the individual classifiers are input features to the ensemble classifier. Based on the input features and training, the ensemble classifier predicts a relationship as the output relationship prediction data in response to predetermined data derived from training the ensemble classifier with a training data set. FIG. 8 shows a Table identifying best classifier in column 805 for classifying a medical relationship identified in column 803 as being of a particular type.

In one embodiment, features A, B, C are extracted from data sources X, Y, Z, respectively. Multiple feature sets are generated using one feature or a combination of features including, S1 using only A, S2 using only B, S3 using only C, S4 using A and B, S5 using B and C, S6 using A and C, S7 using A, B and C FIG. 8 (805) lists a subset of the approximately 40 feature sets generated. Each feature set is capable of outputting and predicting any one of the relationships based on the evidence it sees. That is, for an (e1, e2) entity pair, S1 may predict R2, S2 may predict R3, S3 may predict R3, S4 may predict R2, . . . , S7 may predict R3. The system generates a meta system, SE (ensemble), that uses predictions of all systems, S1, S2, S3, S4, S5, S6, S7, as input, and itself predicts one of the relations R1, R2, R3, as output.

Figure 9:
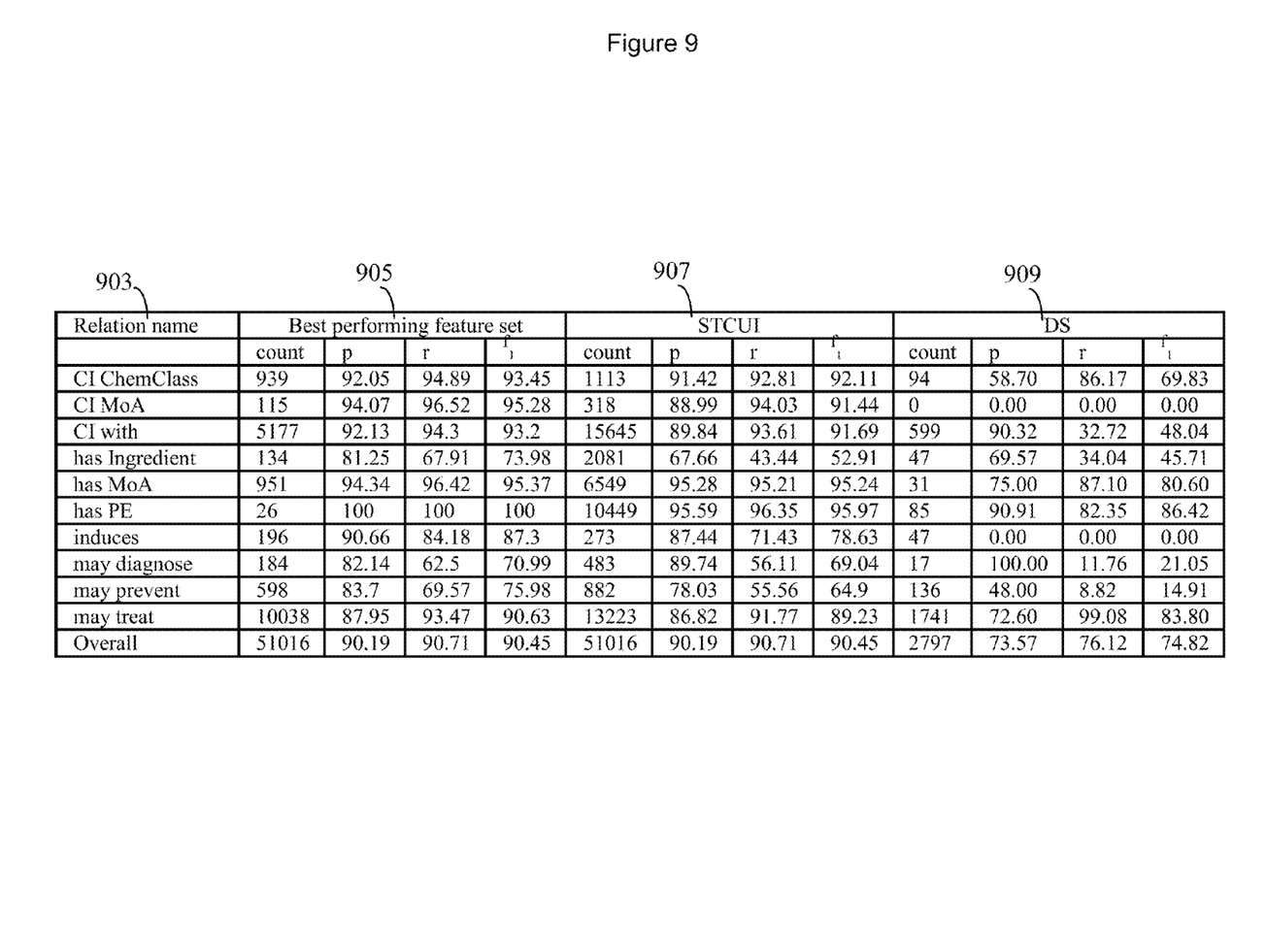
FIG. 9 shows a Table identifying performance of different classifiers trained on training datasets, for classifying different medical relationships between different terms as being of a particular type, according to an embodiment of the invention.

FIG. 9 shows a Table identifying performance of different classifiers trained on training datasets, for classifying different medical relationships between different terms as being of a particular type. Specifically, the Table shows measured performance determined using p, r, f1 values and count values of different classifiers comprising an optimum classifier column 905, STCUI classifier 907 and a DS classifier 909 trained on training datasets, for classifying the medical relationships of column 903 identified between different terms. The ST baseline classifier is omitted as being of relatively low performance. The count values indicate the numbers of instances covered by a specific features set. The system determines a set of biomedical relationships and in one embodiment automatically constructs an ontology and uses classifier ensembles to expand knowledge base coverage.

The system uses multiple different semantic data sources and interrogates Wikipedia, for example, to extract features indicating whether entities of interest are related and determine whether they are in a parent-child relationship and to obtain features indicating the semantic relatedness between terms. The system also uses Wikipedia category and linkage features particularly for biomedical relationship extraction. In the biomedical domain, semantic knowledge is exploited by a classifier using MeSH IDs of words occurring in a sentence and by mapping MeSH subhierarchies to a disease or treatment.

The system performs relationship detection using entity-level semantics and relationship predictions provided by different classifiers using an ensemble method that in one embodiment advantageously operates with minimal data. The system captures medical semantics using a number of resources including Wikipedia, UMLS Semantic Network, MEDCIN, MeSH and SNOMED-CT. Different classifiers are trained using predetermined entities and relationship data. An ensemble system combines use of different predictions. In one embodiment a human-curated ontology is used as a standard to recognize medical relationships of interest.

Figure 10:
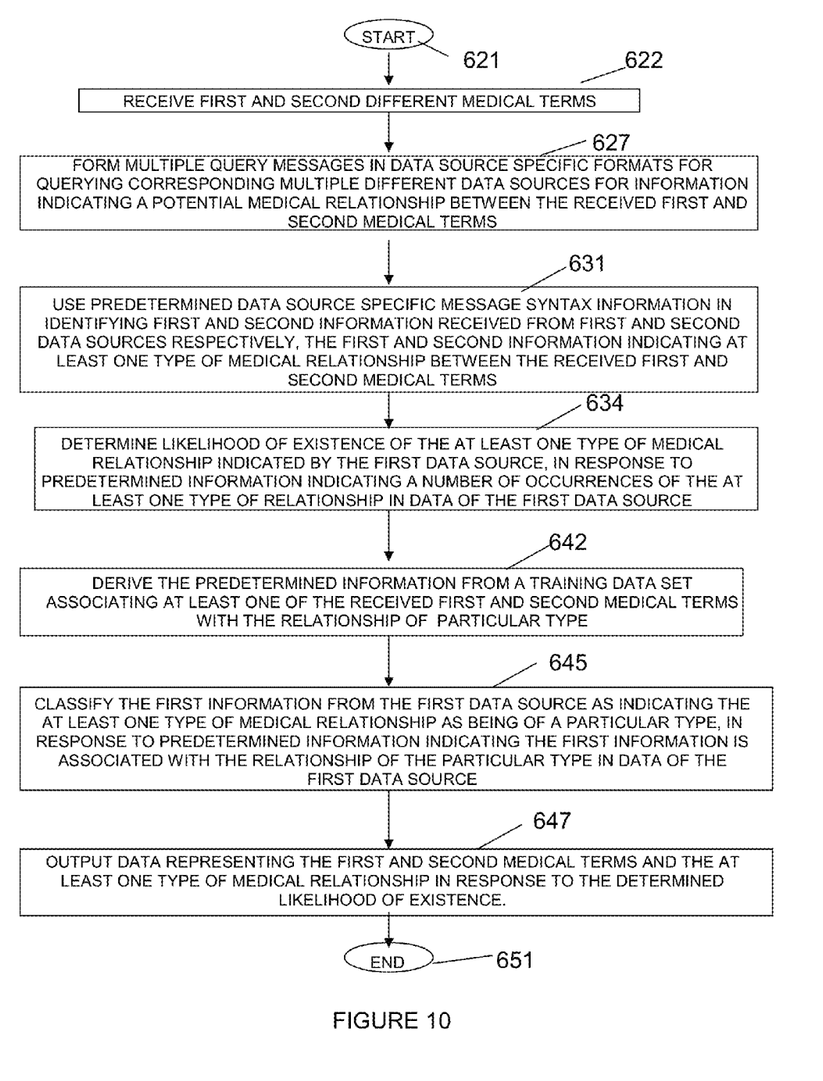
FIG. 10 shows a flowchart of a process performed by a system for generating medical knowledge base information, according to an embodiment of the invention.

FIG. 10 shows a flowchart of a process performed by system 10 (FIG. 2) for generating medical knowledge base information. In step 622 following the start at step 621, data processor 25 receives first and second different medical terms. In step 627, processor 25 forms multiple query messages in data source specific formats for querying corresponding multiple different data sources for information indicating a potential medical relationship between the received first and second medical terms. The data processor receives multiple query response messages in data source specific formats in response to communicating the query messages to the multiple different data sources. Data processor 25 in step 631 uses predetermined data source specific message syntax information in identifying first and second information received from first and second data sources respectively. The first and second information indicates at least one type of medical relationship between the received first and second medical terms. In step 634, processor 25 determines The system determines likelihood of existence of the at least one type of medical relationship indicated by a combination of the first and second information, in response to predetermined information indicating a number of occurrences of the at least one type of relationship in data of at least one of the first and second data source.

In step 642, processor 25 derives the predetermined information from a training data set associating at least one of the received first and second medical terms with the relationship of a particular type. A classifier in processor 25 in step 645 classifies the first information from the first data source as indicating the at least one type of medical relationship as being of a particular type, in response to predetermined information indicating the first information is associated with the relationship of the particular type in data of the first data source and indicating a number of occurrences of the relationship of a particular type in data of the first data source. Processor 25 also identifies the number of occurrences of the particular relationship type between the first term and the different second term in multiple sentences. Further, the classifier classifies the first information as indicating the particular type of relationship, in response to predetermined information indicating a number of occurrences of the particular type of relationship relative to other types of relationship in data of the first data source. Data processor 25 predicts the likelihood of existence of the at least one type of medical relationship in response to the number of occurrences exceeding a predetermined threshold. In one embodiment, the classifier is specifically for classifying relationship data from the first data source.

Data processor 25 includes a second classifier for classifying the second information from the second source as indicating a second medical relationship of a second particular type, in response to predetermined information indicating the second information is associated with the relationship of the second particular type in data of the second data source. The data processor determines whether the at least one type of medical relationship is a medically valid relationship in response to predetermined first and second medical term semantic information received from the first data source and predetermined sentence structure and syntax. Output processor 27 in step 647 outputs data representing the first and second medical terms and the at least one type of medical relationship in response to the determined likelihood of existence. The process of FIG. 10 terminates at step 651.

A processor as used herein is a device for executing machine-readable instructions stored on a computer readable medium, for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a computer, controller or microprocessor, for example, and is conditioned using executable instructions to perform special purpose functions not performed by a general purpose computer. A processor may be coupled (electrically and/or as comprising executable components) with any other processor enabling interaction and/or communication therebetween. Computer program instructions may be loaded onto a computer, including without limitation a general purpose computer or special purpose computer, or other programmable processing apparatus to produce a machine, such that the computer program instructions which execute on the computer or other programmable processing apparatus create means for implementing the functions specified in the block (s) of the flowchart(s). A user interface processor or generator is a known element comprising electronic circuitry or software or a combination of both for generating display images or portions thereof. A user interface comprises one or more display images enabling user interaction with a processor or other device.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A graphical user interface (GUI), as used herein, comprises one or more display images, generated by a display processor and enabling user interaction with a processor or other device and associated data acquisition and processing functions.

The UI also includes an executable procedure or executable application. The executable procedure or executable application conditions the display processor to generate signals representing the UI display images. These signals are supplied to a display device, which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity.

The system and processes of FIGS. 1-10 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. The system automatically discovers medical concepts and relationships that are related to a medical term and determines the type of relationships potentially existing between different terms by mining for knowledge about medical concepts of interest in large (or other) sources of information. Further, the processes and applications may, in alternative embodiments, be located on one or more (e.g., distributed) processing devices on a network linking the units of FIG. 1. Any of the functions and steps provided in FIGS. 1-10 may be implemented in hardware, software or a combination of both. No claim element herein is to be construed under the provisions of 35 U.S.C. 112, sixth paragraph, unless the element is expressly recited using the phrase "means for."

What is claimed is:

1. A system for generating medical knowledge base information, comprising:
    a data processor for, in response to receiving first and second different medical terms, automatically,
        forming a plurality of query messages in data source specific formats,
        querying, using the query messages, a corresponding plurality of different data sources for information indicating a potential medical relationship between the received first and second medical terms,
        using predetermined data source specific message syntax information in identifying first and second information received from first and second data sources respectively, said first and second information indicating at least one type of medical relationship between said received first and second medical terms and
        determining likelihood of existence of said at least one type of medical relationship indicated by a combination of said first and second information, in response to predetermined information indicating a number of occurrences of the at least one type of relationship in data of at least one of said first and second data source; and
    an output processor for outputting data representing said first and second medical terms and the at least one type of medical relationship in response to the determined likelihood of existence.

2. A system according to claim 1, wherein
said combination of said first and second information comprises a concatenation of said first and second information and
said data processor determines whether said at least one type of medical relationship is a medically valid relationship in response to predetermined first and second medical term semantic information received from said first and second data sources.

3. A system according to claim 2, wherein
said data processor determines whether said at least one type of medical relationship is a medically valid relationship in response to predetermined sentence structure and syntax.

4. A system according to claim 1, wherein
said data processor receives a plurality of query response messages in data source specific formats in response to communicating said query messages to said plurality of different data sources.

5. A system according to claim 1, wherein
said data processor includes a classifier for classifying the first information as indicating said at least one type of medical relationship as being of a particular type, in response to predetermined information indicating a number of occurrences of the relationship of a particular type in data of said first data source.

6. A system according to claim 5, wherein said classifier classifies the first information as indicating the particular type of relationship, in response to predetermined information indicating a number of occurrences of the particular type of relationship relative to other types of relationship in data of said first data source.

7. A system according to claim 5, wherein said classifier is specifically for classifying relationship data from said first data source.

8. A system according to claim 1, wherein said data processor includes a first classifier for classifying the first information from said first data source as indicating said at least one type of medical relationship as being of a particular type, in response to predetermined information indicating the first information is associated with the relationship of a particular type in data of said first data source.

9. A system according to claim 8, wherein said predetermined information indicating the first information is associated with the relationship of a particular type, is derived from a training data set associating at least one of the received first and second medical terms with the relationship of said particular type.

10. A system according to claim 8, wherein said data processor includes a second classifier for classifying the second information from said second source as indicating a second medical relationship of a second particular type, in response to predetermined information indicating the second information is associated with the relationship of said second particular type in data of said second data source.

11. A system according to claim 1, wherein said data processor includes a classifier for,
classifying the first information as indicating said at least one type of medical relationship as being of a particular type, in response to predetermined information indicating a number of occurrences of the relationship of a particular type in data of said first data source and
identifies a number of occurrences of the particular relationship type between said first term and said different second term in multiple sentences.

12. A system according to claim 11, wherein said data processor predicts likelihood of existence of said at least one type of medical relationship in response to said number of occurrences.

13. A system according to claim 12, wherein said data processor predicts said likelihood of existence of said at least one type of medical relationship in response to said number of occurrences exceeding a predetermined threshold.

14. A method for generating medical knowledge base information, comprising the steps of:
receiving first and second different medical terms;
forming a plurality of query messages in data source specific formats;
querying, using the query messages, a corresponding plurality of different data sources for information indicating a potential medical relationship between the received first and second medical terms;
using predetermined data source specific message syntax information in identifying first and second information received from first and second data sources respectively, said first and second information indicating at least one type of medical relationship between said received first and second medical terms;
determining likelihood of existence of said at least one type of medical relationship indicated by said first data source, in response to predetermined information indicating a number of occurrences of the at least one type of relationship in data of said first and second data source; and
outputting data representing said first and second medical terms and the at least one type of medical relationship in response to the determined likelihood of existence.

15. A method according to claim 1, including the step of classifying the first information from said first data source as indicating said at least one type of medical relationship as being of a particular type, in response to predetermined information indicating the first information is associated with the relationship of a particular type in data of said first data source.

16. A method according to claim 15, wherein said predetermined information is derived from a training data set associating at least one of the received first and second medical terms with the relationship of said particular type.

17. A method according to claim 14, including the step of determining whether said at least one type of medical relationship is a medically valid relationship in response to predetermined sentence structure semantics rules.

18. A method according to claim 15, including the step of determining whether said at least one type of medical relationship is a medically valid relationship in response to predetermined sentence structure and syntax rules.

19. A method according to claim 14, including the step of receiving a plurality of query response messages in data source specific formats in response to communicating said query messages to said plurality of different data sources.

20. A method according to claim 14, including the step of classifying the first information as indicating said at least one type of medical relationship as being of a particular type, in response to predetermined information indicating a number of occurrences of the relationship of a particular type in data of said first data source.

21. A method according to claim 20, including the step of classifying the first information as indicating the particular type of relationship, in response to predetermined information indicating a number of occurrences of the particular type of relationship relative to other types of relationship in data of said first data source.

* * * * *